United States Patent [19]

Krackov et al.

[11] Patent Number: 4,912,268

[45] Date of Patent: Mar. 27, 1990

[54] PROCESS FOR MANUFACTURE OF FLUOROAROMATICS

[75] Inventors: Mark H. Krackov, Wilmington, Del.; Charles H. Rolston, Woodbury, N.J.

[73] Assignee: E. I. Du Pont De Nemours and Company, Wilmington, Del.

[21] Appl. No.: 263,952

[22] Filed: Oct. 21, 1988

Related U.S. Application Data

[63] Continuation-in-part of Ser. No. 161,024, Feb. 26, 1988, abandoned.

[51] Int. Cl.$^4$ .................... C07C 17/22; C07C 25/13
[52] U.S. Cl. ...................................................... 570/141
[58] Field of Search ......................................... 570/141

[56] References Cited

U.S. PATENT DOCUMENTS

| | | | |
|---|---|---|---|
| 2,563,796 | 8/1951 | Shenk et al. | 260/650 |
| 3,471,511 | 10/1969 | Kollonitsch | 260/309 |
| 3,471,512 | 10/1969 | Kollonitsch et al. | 260/309 |
| 3,573,214 | 3/1971 | Kollonitsch et al. | 252/182 |
| 3,798,228 | 3/1974 | Boudakian et al. | 260/290 |
| 3,950,444 | 4/1976 | Gay | 260/650 |
| 4,075,252 | 2/1978 | Boudakian | 260/649 |
| 4,096,196 | 6/1978 | Boudakian | 260/650 |
| 4,145,364 | 3/1979 | Mulvey et al. | 260/578 |
| 4,423,260 | 12/1983 | Christe et al. | 570/147 |
| 4,476,320 | 10/1984 | Diehl et al. | 560/103 |

FOREIGN PATENT DOCUMENTS

| | | |
|---|---|---|
| 600706 | 3/1933 | Fed. Rep. of Germany . |
| 2113253 | 3/1971 | Fed. Rep. of Germany . |
| 8133074 | 5/1978 | Japan . |

OTHER PUBLICATIONS

JACS 72, 4809 by Ferm and Vander Werf (1950).
U.S. Pat. No. 4,194,054–Abstract–Claim 1.

*Primary Examiner*—J. E. Evans
*Attorney, Agent, or Firm*—Charles E. Krukiel

[57] ABSTRACT

Process which comprises feeding an aromatic amine in the presence of HF to a reaction zone simultaneously with a diazotizing agent so as to effect diazotization of the aromatic amine, thermally decomposing the resulting diazonium salt substantially as it is formed, and removing the resulting fluoroaromatic compound from the reaction zone substantially as it is formed. The amine and the diazotizing agent are fed to the reaction zone in such quantities and proportions that they are consumed substantially as fed so that no substantial concentration of either builds up in the reaction zone.

20 Claims, No Drawings

PROCESS FOR MANUFACTURE OF FLUOROAROMATICS

This application is a continuation-in-part of application Ser. No. 161,024, filed Feb. 26, 1988, now abandoned.

FIELD OF THE INVENTION

The present invention relates to the manufacture of fluoroaromatics by diazotizing an aromatic amine in HF, and decomposing the resulting aryldiazonium fluoride as it is formed. It relates particularly to the manufacture of fluorobenzene from aniline.

BACKGROUND OF THE INVENTION

It is known to manufacture fluoroaromatics by diazotizing an aromatic amine, such as aniline, in anhydrous HF, usually at 0° C., followed by thermal decomposition of the aryldiazonium fluoride. Osswald et al., German Pat. No. 600,706, disclose a two-step process in which sodium nitrite is added to a cold solution of the aromatic amine in anhydrous HF. The reaction mixture is then heated to decompose the diazonium fluoride to give nitrogen and the aromatic fluoride. Misaki et al. in Japanese Patent Publication No. 81330/74, disclose a one-step process wherein the diazotization agent, such as sodium nitrite, in anhydrous HF is fed to a solution of the aromatic amine in anhydrous HF at a sufficiently high temperature (30°–50° C.) that diazotization and decomposition of the diazonium fluoride occur simultaneously. The reaction mass is then cooled, the organic layer allowed to separate and the product isolated by steam distillation. In U.S. Pat. No. 4,075,252, Boudakian claims enhanced yields when ammonium ions are present in the reaction medium, and in U.S. Pat. No. 4,096,196, claims enhanced yields when selected tertiary amines are present. Following the reaction, the reaction mass is cooled, the phases separated, the organic phase neutralized with caustic and the crude fluoroaromatic product steam-distilled. Either of these concepts can be practiced using the one- or two-step processes described above.

SUMMARY OF THE INVENTION

The present invention relates to a process for preparing a fluoroaromatic compound which comprises feeding an aromatic amine in the presence of HF to a reaction zone simultaneously with a diazotizing agent so as to effect diazotization of the aromatic amine, thermally decomposing the resulting diazonium salt substantially as it is formed, and removing the resulting fluoroaromatic compound from the reaction zone substantially as it is formed. The amine and the diazotizing agent are fed to the reaction zone in such quantities and proportions that they are consumed substantially as fed so that no substantial concentration of either builds up in the reaction zone.

DETAILED DESCRIPTION OF THE INVENTION

The process of the present invention can be represented by the following balanced equation using $N_2O_3$ as the diazotization agent:

$$2\,R\text{—}(NH_2)_n + n\,N_2O_3 + 2n\,HF \longrightarrow 2\,R\text{—}(N_2{}^+F^-)_n + 3n\,H_2O$$

-continued

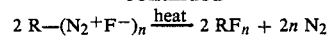

wherein R is an aromatic radical, such as phenyl, tolyl, chlorophenyl, chlorotolyl, nitrophenyl, phenylene, and the like, and n is 1 or 2. The aromatic amine in HF reacts rapidly with the diazotization agent to produce the aryldiazonium fluoride which thermally decomposes substantially as it is formed to produce an aromatic fluoride. The aromatic amine and the diazotization agent are fed simultaneously in such quantities and proportions that no substantial concentration of either the amine or the diazotizing agent builds up in the reaction zone. The crude product may be removed as it is formed from the reaction zone either by vapor phase stripping in an inert gas stream (hereinafter referred to as flashing) or by extraction into an inert liquid phase which is immiscible with the reaction mass. In most cases, where the product is sufficiently volatile, flashing will be the preferred means of product removal. The flashed crude product contains the desired fluoroaromatic compound, HF, and a trace amount of fluorobiphenyls. The reaction mass which remains behind contains HF, most of the water produced in the reaction, fluorobiphenyls, ammonium bifluoride and non-volatile organic by-products. The amount of fluorobiphenyls formed in the reaction is less than that obtained when the prior art process is used, because of the fluoroaromatic product having been removed from the reaction mass as formed. On the other hand, little or no carcinogenic aminobiphenyls (or similar aminoaromatic compounds) are formed, because the aromatic amine reactant is consumed in the diazotization reaction substantially as fed to the reaction mass.

Suitable aromatic amines include aniline; o-, m- or p-toluidine; m- or p-nitroaniline; o-, m- or p-chloroaniline; m-phenylene diamine; the chlorotoluidines; and their hydrochloride and hydrofluoride salts. The aromatic amines are dissolved in anhydrous HF to make a solution which is fed into the reaction zone. The upper limit to the concentration of the amine in solution varies with the solubility of the amine; the lower limit is simply a matter of convenience. Suitably, from about a 1% by weight to a 60% by weight solution of the amine in HF can be used. A solution containing about 43.7% by weight of amine in anhydrous HF is preferred. The usual diazotizing agents, namely sodium nitrite, potassium nitrite, nitrogen trioxide (nitrous anhydride), nitrous acid and nitrosyl halides or nitrosyl halide complexes with HF can be employed in the reaction. In addition, any combination of reagents capable of forming a diazotizing agent, such as combinations of NO and $O_2$, can be used. A carrier gas, such as $N_2$ can also be used. Preferably, between about 1.1 and 1.5 equivalents of diazotizing agent per equivalent of aromatic amine should be used. The solid and liquid diazotizing agents are dissolved in anhydrous HF to make a solution which is fed into the reactor. The concentration of the solution depends on the molecular weight and solubility of the diazotizing agent in HF. A gaseous diazotizing agent may be fed directly into the reactor.

When the fluoroaromatic product and HF have about the same density, they can be separated from one another in the flashed crude product by the addition of a material which increases or decreases the density of either phase relative to the other. Materials which will increase the density of the HF phase include water, any salt, such as ammonium bifluoride, and the like. On the other hand, an HF-immiscible organic solvent can be added to the crude product so as to reduce or increase the density of the organic phase and thereby facilitate separation of the two phases. After separation of the two phases, the organic phase is washed and dried. Ammonium bifluoride can be formed in situ by adding anhydrous ammonia to HF. It is preferred for the purpose of increasing the density of the HF phase, because it can be recycled with the HF to the reaction mass.

With fluoroaromatic products which exert low vapor pressures under the conditions of the reaction, the preferred method for removal of the product from the reaction zone may be by extraction into an inert liquid phase which is immiscible with the reaction mass. This extraction has been successfully carried out both in the reactor (wherein the inert liquid phase may be considered to constitute a zone separate and distinct from the reaction zone) and also outside the reactor, by continuously circulating the reaction mass from the reactor into a continuous liquid/liquid separator and thence back to the reactor. As is the case with flashing, continuous removal of the product as formed produces increased product yields and decreased by-product formation. The extracting solvent may be any organic material which is inert under the conditions of the reaction, immiscible with HF, has good solubility for the fluoroaromatic product, and is easily separated from the product, say by distillation. Among solvents which have been successfully employed are decahydronaphthalene and dodecane.

It has been found in a preferred embodiment that the addition of ammonium ions to the reaction mixture modestly increases the product yield. Common sources of ammonium ions can be found in commercial sources such as but not limited to anhydrous ammonia in HF, ammonium bifluoride, ammonium acetate, ammonium bicarbonate, ammonium chloride and ammonium sulfate. The amount of ammonium ion is most conveniently expressed as a molar percentage of the solution of hydrogen fluoride. It can range from about 0.5 to about 35 percent of the HF solution, preferably from about 2.5 to about 15 molar percent of the HF solution. For purposes of determining these percentages, ammonium bifluoride is regarded as contributing one mole of HF and one mol of ammonium ion per mol of the bifluoride.

In accordance with the invention, no external heat is necessary, provided that the heat generated from the reaction is above the minimum temperature for decomposition of the diazonium fluoride. However, it is advantageous to supply heat to the reaction, both to minimize reaction time and build-up of the diazonium salt. In decomposing the benzenediazonium fluoride prepared from aniline, a temperature of at least about 35° C. is advantageous. The upper temperature limit is dictated by the boiling point of the reaction mass which depends on the salt and water content as well as pressure. It is convenient to operate at a temperature in the range of 52°-55° C. But the process has been operated at 100° C. (with fluoroaromatics other than benzene and with additional $NH_4HF_2$ to increase the boiling point of the reaction mass).

The process of this invention can be run in a semi-batch or continuous mode. In the semi-batch mode, a solution of ammonium bifluoride in HF is fed to the reaction vessel and heated to the desired reaction temperature. Then in one case, a solution of the aromatic amine starting material in HF and a solid diazotizing agent in solution in HF are metered into the reaction vessel. When a gaseous diazotizing agent is used, it is sparked directly into the reaction vessel. The product is then removed from the reaction mass by flashing or by solvent extraction. In continuous operation, the volume of the reaction mass is held constant by continuous overflow of the reaction mass. In the semi-batch mode using $NO_x$ as the diazotizing agent, the solution of the amine in HF is fed to the top of the reaction vessel countercurrent to the HF solution of the diazotizing agent which is fed to the bottom of the vessel. In continuous operation, the HF solutions of the amine and the diazotizing agent are both fed concurrently from the bottom of the reaction vessel. The process can be run at atmospheric and elevated pressures.

The process of this invention leads to improvements in product yield and quality. A four- to five-fold reduction in the formation of by-product fluorobiphenyls (which can co-distill with the product and cause pluggage of vent and condensate lines) leads to ease of product isolation. A large reduction in, or elimination of, by-product p-aminobiphenyl enables one to reduce or eliminate any need to handle a waste stream containing a potent carcinogen. Removal of the product by flashing produces additional improvements in process operability as the heat evolved during the diazotization and decomposition steps can be used to remove the product as it is formed. That provides valuable process temperature control and significantly reduces the refrigeration requirements of the process. The product is easily separated from anhydrous HF which co-distills with it, washed with aqueous NaOH, and dried without redistillation or any other additional purification steps. When fluorobenzene is made from aniline by the process of this invention, 99.5% of the product can be flashed from the reactor as it is formed with an organic purity in excess of 99.9%.

The following Examples are illustrative of the invention.

EXAMPLE 1 (Best Mode)

The apparatus consisted of a 33 inch by 4 inch ID tubular reactor lined with a TEFLON ® fluoropolymer, an external recirculation loop, internal baffles made of a TEFLON ® fluoropolymer, and a pump to provide circulation through a process heater/cooler located in the external loop. HF/aniline feed was to the top of the reactor, countercurrent to the gas feed located in the bottom of the reactor. The reactor was connected to an overhead brine-cooled condenser and receiver for recovery of flashed material. An overflow line and receiver were also incorporated in the apparatus to allow continuous overflow of the reaction mass. The working volume of the reactor was determined to be 1.93 gallons.

A "heel" of 4.66 lbs $NH_4HF_2$ and 9.34 lbs anhydrous HF was pumped to the reactor and heated to 50° C. A solution of 33.1% aniline and 8.9% $NH_4HF_2$ in HF was metered to the reactor at a rate of 2.07 lbs (0.0223 lb mols) of aniline per hour; simultaneously a gas mixture of nitric oxide (4 parts by volume), oxygen (1 part by volume), and nitrogen (1 part by volume) was sparged into the bottom of the reactor at a total gas feed rate of 1.5 lbs per hour, equivalent to a nitrous anhydride feed rate of 0.0167 lb mol per hour. The reactants were fed to the reactor at constant rates for a period of 8 hours while maintaining the reactor temperature at 52°-53° C.

Simultaneously, the reaction mass overflowed from the reactor at a rate sufficient to maintain a constant operating volume. During the 8 hour reaction period, the aniline was diazotized and the resulting benzenediazonium fluoride decomposed as formed, leading to the formation of fluorobenzene. As it was formed, the fluorobenzene was flashed out of the reaction mass, condensed and collected in the product receiver, and separated from HF with which it co-distilled, by the addition of toluene to the product receiver. Using internal standards, the organic layer was analyzed by gas chromatography to determine the fluorobenzene content. In a 1 hour period under steady state conditions, a yield of 1.91 lbs fluorobenzene (89.2% of theory) was recovered in the receiver. Analysis of reactor overflow material disclosed no aniline, indicating 100% aniline conversion in the reactor. Filtration of samples from the reactor overflow showed 1–2% by weight of nonvolatile organic by-products.

EXAMPLE 2

The apparatus consisted of a 12-inch by 2-inch (I.D.) fluoropolymer-lined steel tubular reactor fitted with internal tetrafluoroethylene polymer baffles, thermocouple, bottom-inlet gas sparger and an external pump-fed recirculation loop into which aniline/HF was metered (counter-current to the gas feed). The reactor, fitted with external heating coils, was connected via a hot tube to a brine-cooled take-off condenser, receiver, scrubber and gas flow meters. A "heel" of 100 g of ammonium bifluoride in 200 g of anhydrous HF was pumped into the reactor and heated to approximately 50° C. A solution of 43.7% aniline in HF was then pumped into the reactor at a rate of 0.529 g (5.68 mmols) of aniline per minute; simultaneously a gas mixture prepared by mixing nitric oxide (4 parts by volume), oxygen (1 part by volume) and nitrogen (1 part by volume) was sparged into the reactor at a rate of 150 cc/min, equivalent to a nitrous anhydride feed rate of 4.46 mmols/min. With the reactor temperature maintained at 52°–55° C., the reactants were fed for a period of 133 minutes, during which time diazotization of the aniline and decomposition of the resulting benzenediazonium fluoride led to formation of fluorobenzene, which was flashed out of the reaction mass as it was formed and collected in the product receiver. The crude flash-distilled fluorobenzene was separated from HF, with which it co-distills, by the addition of ammonium bifluoride to the mixture and decantation of the upper organic phase. The washed and dried product was obtained with a yield of 60.03 g (83.2% of theory, based on aniline) and a chromatographic purity of 99.91%. Total isomeric fluorobiphenyls formed in the process was 0.11 g (0.17% of theory); no p-aminobiphenyl (p-ABP) was detected. Non-volatile organic by-products weighed 3.08 g.

CONTROL 1

The apparatus was as described in Example 2 except that a brine-cooled reflux condenser was placed above the reactor. Ammonium bifluoride (100 g), HF (200 g) and aniline (69.9 g, 0.75 mol) were charged to the reactor. The reactor contents were then heated to 50° C. and $NO_x$ sparged into the reactor for 135 minutes, as described above. Then the reaction mass was cooled to room temperature and the contents quenched in a mixture of toluene and ice water. The organic phase, containing the product fluorobenzene, was separated from the aqueous layer, washed, dried and analyzed chromatographically. The yield of fluorobenzene was 40.14 g (55.7% of theory). Chromatographic purity was 92%. Isomeric fluorobiphenyls and other high-boiling organic species formed in the process totaled 3.23 g (5.0% of theory), including about 1 mg of p-ABP. Non-volatile organic by-products weighed 5.43 g.

EXAMPLE 3

The apparatus consisted of a 500 ml Teflon ® fluoropolymer vessel fitted with a thermocouple, magnetic stirrer and inlet tubes for feeding the reactants. The reaction vessel was immersed in a thermostatted water bath for external heating and was connected via a hot tube to a brine-cooled take-off condenser, receiver, scrubbers and gas flow meters. A "heel" of 14.3 g of ammonium bifluoride in 30.0 g of anhydrous HF was charged to the reaction vessel and heated to approximately 50° C. Into this heel were then simultaneously metered a solution of 43.7% aniline in anhydrous HF and a solution of 24.1% $NaNO_2$ in anhydrous HF, the feed rates being so adjusted that 23.3 g (0.25 mol) of aniline was fed in 45 minutes and the ratio of $NaNO_2$:aniline was 1.1:1.0. Throughout the course of the run, the temperature was controlled at 52°–55° C., and product fluorobenzene was removed as it was formed by flash distillation. The crude flash-distilled fluorobenzene was separated from HF, with which it codistills, washed and dried. The yield of product was 19.6 g (81.7% of theory, based on aniline); purity as determined by gas chromatography was 99.84%. Isomeric fluorobiphenyls formed in the process totaled 0.37 g (1.5% of theory). Approximately 1 mg of p-ABP was formed. Non-volatile organic by-products weighed 1.56 g.

CONTROL 2

The apparatus was as described in Example 3 except that a brine-cooled reflux condenser was placed above the reactor. Ammonium bifluoride (14.3 g), HF (35 g) and aniline (23.3 g, 0.25 mol) were charged to the reactor and heated to approximately 50° C. Into this mixture was then metered a solution of 19.0 g (0.275 mol) of sodium nitrite in 60 g HF, over a period of 45 minutes. The reaction mass was then cooled to room temperature and the contents of the reactor worked up as described in Control 1. The yield of fluorobenzene was 17.0 g (71.3% of theory, based on aniline). Chromatographic purity was 95%. Total isomeric fluorobiphenyls and other high-boiling organic by-products formed in the process totaled 0.92 g (3.7% of theory), including approximately 5 mg of p-ABP. Non-volatile organic by-products weighed 1.38 g.

EXAMPLE 4

The apparatus employed was that described in Example 2. A "heel" of 100 g of ammonium bifluoride in 200 g of anhydrous HF was pumped into the reactor and heated to approximately 60° C. A solution of 47.2% p-toluidine in anhydrous HF was then pumped into the reactor at a rate of 0.597 g (5.57 mmols) of toluidine per minute; simultaneously a gas mixture prepared by mixing nitric oxide (3.6 parts), oxygen (0.9 part) and nitrogen (1 part) was sparged into the reactor at a rate of 140 cc/min, equivalent to a nitrous anhydride feed rate of 4.02 mmol/min. With the reactor temperature maintained at 60°–64° C., the reactants were fed for a period of 135 minutes, during which time diazotization of the toluidine and decomposition of the resulting diazonium fluoride salt led to formation of p-fluorotoluene, which was flashed out of the reaction mass as it was formed and collected in the product receiver. The crude flash-distilled product was collected, washed and dried as described in Example 2. The yield of p-fluorotoluene was 57.8 g (69.8% of theory, based on toluidine); chromatographic purity was 99.93%.

CONTROL 3

The apparatus was as described in Example 2 except that a brine-cooled reflux condenser was placed above the reactor. Ammonium bifluoride (150 g), HF (300 g) and p-toluidine (80.4 g, 0.75 mol) were charged to the reactor. The reactor contents were then heated to 60° C. and a mixture of $NO_X$-nitrogen sparged into the reactor at a rate equivalent to 4.46 mmol/min of nitrous anhydride. After 126 minutes, the reaction mass was cooled to room temperature and the contents worked up as described in Control 1. The yield of p-fluorotoluene was 27.1 g (32.8% of theory). Chromatographic purity was 88.6%. By-products formed included 5.1 g of high-boiling ring-nitrated products and 7.4 g of nonvolatile organic solids. In addition, 10.55 g (13.1%) of unreacted p-toluidine were recovered.

EXAMPLE 5

The apparatus and procedures were as described in Example 2, except that the "heel" pumped to the reactor contained 100 g of ammonium bifluoride dissolved in 222 g of 90% aqueous HF. The washed and dried fluorobenzene product was obtained with a yield of 59.64 g (82.7% of theory, based on aniline) and a chromatographic purity of 99.94%. Total isomeric fluorobiphenyls formed in the process was 0.06 g (0.10% of theory); no p-aminobiphenyl was detected.

EXAMPLE 6

The apparatus and procedures were as described in Example 5, except that the reactor temperature was maintained at 66°-70° C. throughout the course of the reaction. The washed and dried fluorobenzene product was obtained with a yield of 59.85 g (83.0% of theory, based on aniline) and a chromatographic purity of 99.56%. Total isomeric fluorobiphenyls formed in the process was 0.27 g (0.45% of theory); no p-aminobiphenyl (p-ABP) was detected. Non-volatile organic by-products weighed 0.67 g.

EXAMPLE 7

The apparatus and procedures were as described in Example 2, except that the "heel" pumped to the reactor contained 62.6 g of sodium fluoride dissolved in 200 g of anhydrous HF. The washed and dried fluorobenzene product was obtained with a yield of 53.28 g (74.0% of theory, based on aniline and a chromatographic purity of 99.89%. Total isomeric fluorobiphenyls formed in the process was 0.06 g (0.10% of theory); no p-aminobipheyl (p-ABP) was detected. Non-volatile organic by-products weighed 8.18 g.

EXAMPLE 8

The apparatus employed was similar to that described in Example 2, modified to permit continuous operation by incorporation of a reactor overflow line with receiver. The overflow line was located so as to allow operation at a constant reactor volume of 600 ml. The reaction mass was circulated through an external loop, into which the aniline/HF/NH$_4$HF$_2$ feed was metered concurrently with the gas feed.

A "heel" of 168 g of NH$_4$HF$_2$ and 98 g of water in 539 g of anhydrous HF was pumped into the reactor and heated to 50 C. A solution of 32.3% aniline and 8.9% NH$_4$HF$_2$ in anhydrous HF was then pumped into the reactor at a rate of 0.529 g (5.68 mmols) of aniline per minute; simultaneously, a gas mixture prepared by mixing nitric oxide (4 parts), oxygen (1 part), and nitrogen (1 part) was sparged into the reactor at a rate of 150 cc/min., equivalent to a nitrous anhydride feed rate of 4.46 mmols/min. With the reactor temperature maintained at 54°-56° C., the reactants were fed for a period of 1360 min., to achieve steady-state operation, during which time diazotization of the aniline and decomposition of the resulting benzenediazonium fluoride led to formation of fluorobenzene, which was flashed out of the reaction mass as it was formed and collected in the product receiver. Simultaneously, the reaction mass, containing 0.02% of fluorobenzene, was discharged from the reactor at a rate sufficient to maintain a constant operating volume.

The crude flash-distilled fluorobenzene was collected and treated as described in Example 2. In a 2-hour period under conditions of steady-state operation, the washed and dried product was obtained with a yield of 54.37 g (83.0% of theory); chromatographic purity was 99.94%. Isomeric fluorobiphenyls formed during the same period amounted to 0.06 g (0.09% of theory); no p-aminobiphenyl was detected. Total non-volatile organic by-products formed during the entire run weighed 2.76 g.

EXAMPLE 9

Fluorobenzene, batch, N$_2$O$_3$, simultaneous feed, product removal by external extraction.

The apparatus employed was that described in Example 2, but was modified as follows: (a) the hot tube leading from the reactor to the take-off condenser was replaced by a brine-cooled reflux condenser, and (b) a side stream of the reaction mass was circulated continuously from the reactor into a continuous liquid/liquid extractor and thence back to the reactor. The extractor was filled with dodecane to a constant (overflow) volume and recharged continuously with fresh extractant.

A "heel" of 180 g of ammonium bifluoride in 300 g of anhydrous HF was pumped into the reactor and heated to approximately 50° C. A solution of 43.7% aniline in HF was then pumped into the reactor at a rate of 0.375 g (4.02 mmols) of aniline per minute; simultaneously a gas mixture prepared by mixing nitric oxide (3.6 parts by volume) was sparged into the reactor at a rate of 102 cc/min, equivalent to a nitrous anhydride feed rate of 3.02 mmols/min. With the reactor temperature maintained at 52°-59° C., the reactants were fed for a period of 139 minutes, during which time diazotization of the aniline and decomposition of the resulting benzenediazonium fluoride led to formation of fluorobenzene, which was continuously extracted from the reaction mass as it was formed. The total yield of fluorobenzene, which may be separated from the dodecane extractant by distillation, was 44.6 g (82.9% of theory); total isomeric fluorobiphenyls formed in the process was 0.08 g (0.15% of theory). Nonvolatile organic by-products weighted 1.88 g.

EXAMPLE 10

2-Chloro-4-fluorotoluene, batch, N₂O₃, simultaneous feed, product removal by internal extraction.

The apparatus employed was that described in Example 2, but with the hot tube leading from the reactor replaced by a brine-cooled reflux condenser. A "heel" of 200 g of ammonium bifluoride in 200 g of anhydrous HF was pumped together with 150 g of dodecane into the reactor at a rate of 0.776 g (5.48 mmols) of the amine per minute; simultaneously a gas mixture prepared by mixing nitric oxide (3.6 parts by volume), nitrogen (1 part), and oxygen (0.9 part) was sparged into the reactor at a rate of 142 cc/min, equivalent to a nitrous anhydride feed rate of 4.11 mmols/min. With the reactor temperature maintained at 80°–96° C., the reactants were fed for a period of 139 minutes, during which time diazotization of the chlorotoluidine and decomposition of the resulting diazonium fluoride salt led to formation of 2-chloro-4-fluorotoluene, which was extracted as formed out of the reactive medium and into the dodecane phase. The total yield of the product chlorofluorotoluene, which may be separated from the dodecane extractant by distillation, was 91.0 g (82.6% of theory).

CONTROL 4

2-Chloro-4-fluorotoluene, batch, N₂O₃, simultaneous feed, no product removal.

The apparatus employed was that described in Example 10. A "heel" of 160 g of ammonium bifluoride in 200 g of anhydrous HF was pumped into the reactor and heated to approximately 80° C. A solution of 53.8% 3-chloro-4-methylaniline in HF was then pumped into the reactor at a rate of 0.792 g (5.59 mmols) of the amine per minute; simultaneously a gas mixture prepared by mixing nitric oxide (3.6 parts by volume), oxygen (0.9 part) and nitrogen (1 part) was sparged into the reactor at a rate of 140 cc/min. With the reactor temperature maintained at 80°–86° C., the reactants were fed for a period of 135 minutes, during which time diazotization of the chlorotoluidine and decomposition of the resulting diazonium fluoride salt led to formation of 2-chloro-4-fluorotoluene. The reaction mass, containing the product, was cooled to room temperature and the contents of the reactor worked up as described in Control 1. The total yield of 2-chloro-4-fluorotoluene was 74.5 g (68.7% of theory).

We claim:

1. A process for preparing a fluoroaromatic compound comprising (a) in the presence of HF and at a temperature sufficient to effect decomposition of the resulting aryldiazonium fluoride, feeding an aromatic amine to a reaction zone simultaneously with a diazotizing agent in such quantities and proportions that no substantial concentration of either the amine or the diazotizing agent builds up in the reaction zone, (b) thermally decomposing the resulting diazonium salt substantially as it is formed, and (c) removing the resulting fluoroaromatic compound from said reaction zone substantially as it is formed.

2. The process of claim 1 wherein said aromatic amine is aniline and said fluoroaromatic compound is fluorobenzene.

3. The process of claim 2 wherein said diazotizing agent is nitrogen trioxide.

4. The process of claim 2 wherein said diazotizing agent is sodium nitrite.

5. The process of claim 2 wherein said fluoroaromatic compound is removed from said zone by flashing.

6. The process of claim 5 wherein heat evolved in said diazotization and decomposition steps is used to effect flashing of said fluoroaromatic compound.

7. The process of claim 2 wherein said fluoroaromatic compound is removed from said zone by extraction.

8. The process of claim 2 wherein said diazotization and decomposition steps are conducted in a solution of HF containing ammonium ions.

9. The process of claim 8 wherein said HF solution contains ammonium bifluoride.

10. The process of claim 1 wherein said aromatic amine is p-toluidine and said fluoroaromatic compound is p-fluorotoluene.

11. A continuous process for preparing a fluoroaromatic compound comprising (a) in the presence of HF and at a temperature sufficient to effect decomposition of the resulting aryldiazonium fluoride, continuously feeding an aromatic amine to a reaction zone simultaneously with an approximate stoichiometric proportion of a diazotizing agent so as to effect diazotization, (b) continuously decomposing the resulting diazonium salt substantially as it is formed, and (c) continuously removing the resulting fluoroaromatic compound from the reaction zone substantially as it is formed.

12. The process of claim 11 wherein said aromatic amine is aniline and said fluoroaromatic compound is fluorobenzene.

13. The process of claim 12 wherein said diazotizing agent is nitrogen trioxide.

14. The process of claim 12 wherein said diazotizing agent is sodium nitrite.

15. The process of claim 12 wherein said fluoroaromatic compound is removed from said zone by flashing.

16. The process of claim 15 wherein heat evolved in said diazotization and decomposition steps is used to effect flashing of said fluoroaromatic compound.

17. The process of claim 12 wherein said fluoroaromatic compound is removed from said zone by extraction.

18. The process of claim 12 wherein said diazotization and decomposition steps are conducted in a solution of HF containing ammonium ions.

19. The process of claim 18 wherein said HF solution contains ammonium bifluoride.

20. The process of claim 11 wherein said aromatic amine is p-toluidine and said fluoroaromatic compound is p-fluorotoluene.

* * * * *